United States Patent [19]
Camden

[11] Patent Number: 6,090,796
[45] Date of Patent: *Jul. 18, 2000

[54] PHARMACEUTICAL COMPOSITION FOR INHIBITING THE GROWTH OF CANCERS

[75] Inventor: James Berger Camden, West Chester, Ohio

[73] Assignee: The Procter & Gamble Company, Cincinnati, Ohio

[ * ] Notice: This patent is subject to a terminal disclaimer.

[21] Appl. No.: 09/220,914

[22] Filed: Dec. 24, 1998

Related U.S. Application Data

[63] Continuation of application No. 08/680,469, Jul. 15, 1996, Pat. No. 5,854,231, which is a continuation-in-part of application No. 08/420,940, Apr. 12, 1995, Pat. No. 5,665,713.
[60] Provisional application No. 60/001,840, Aug. 3, 1995.

[51] Int. Cl.⁷ .................... A01N 57/00; C07D 265/30; C07D 211/36; C07D 207/12
[52] U.S. Cl. ......................... 514/89; 514/75; 514/91; 544/173; 546/242; 548/541; 548/542; 548/543; 556/18; 556/19
[58] Field of Search ............ 544/173; 546/242; 548/541, 542, 543; 556/18, 19; 514/89, 91, 75

[56] References Cited

U.S. PATENT DOCUMENTS

| | | | |
|---|---|---|---|
| 3,799,758 | 3/1974 | Franz | 71/86 |
| 3,853,530 | 12/1974 | Franz | 71/76 |
| 3,903,297 | 9/1975 | Robert | 424/305 |
| 4,408,052 | 10/1983 | Hozumi et al. | 546/22 |
| 4,542,219 | 9/1985 | Hozumi et al. | 546/22 |
| 4,544,512 | 10/1985 | Hozumi et al. | 260/925 |
| 4,634,693 | 1/1987 | Cordelli | 514/169 |
| 4,649,203 | 3/1987 | Nojima et al. | 548/112 |
| 4,775,758 | 10/1988 | Nojima et al. | 546/22 |
| 4,866,059 | 9/1989 | Temple, Jr. | 514/248 |
| 4,994,591 | 2/1991 | Anderson | 556/169 |
| 5,114,951 | 5/1992 | King | 514/290 |
| 5,854,231 | 12/1998 | Camden | 514/76 |

OTHER PUBLICATIONS

Registry compound no. #25316–40–9, adriamycin, 1999.
Registry compound no. #1071–83–6, glyphosate, 1999.
Dus, "Cytostatic Activity in vitro of Phosphonic Acid Derivatives," Archivum Immunologiae et Therapiae Experimentalis, 325–329 (1985).
Mochida, "Chemical Control of Green Leafhoppers to Prevent Virus Diseases, Especially Tungro Disease, on susceptible/Intermediate Rice Cultivars in the Tropics," Tropical Agricultural Research, vol. 19, 195–208 (1985).
Bandurina, "Synthesis of Antitumor Activity of Aminophosphonic Acids," Pharmaceutical Chemistry Journal, vol. 12, No. 11, 35–37 (Nov. 1978), 1988.
Dorr, et al 2$^{nd}$ Chapter, Cancer Chemotherapy Handbook, Chapter 2 (Appleton & Lange, Conn.) pp 15–34 (1994).
Chemical Abstracts #123:248848, abstract of Mumtoz, Toxicol. Lett (1995), vol. 79, (1–3) pp 131–143.

*Primary Examiner*—D. Margaret Seaman
*Attorney, Agent, or Firm*—Rose Ann Dabek; Jacobus C. Rasser

[57] ABSTRACT

This invention is a pharmaceutical composition that inhibits the growth of cancers and tumors in mammals, particularly in human and warm blooded animals. The composition contains N-phosphonoglycine derivatives which are systemic herbicides in combination with chemotherapeutic agents for treatment of cancers and tumors. N-phosphonoglycine derivatives can be used to treat viral infections, particularly herpes infections. Optionally potentiators can be included.

26 Claims, No Drawings

PHARMACEUTICAL COMPOSITION FOR INHIBITING THE GROWTH OF CANCERS

This is a continuation of application Ser. No. 08/680,469, filed on Jul. 15, 1996, now U.S. Pat. No. 5,854,231 which is a cip of Ser. No. 08/420,940, filed Apr. 12, 1995, now U.S. Pat. No. 5,665,713 which claims benefits of provisional application 60/001,840 Aug. 3, 1995.

TECHNICAL FIELD

This invention is a pharmaceutical composition that inhibits the growth of cancers and tumors in mammals, particularly in human and warm blooded animals. The composition is also effective against viruses. The composition contains N-phosphonoglycine derivatives which are systemic herbicides.

BACKGROUND OF THE INVENTION

Cancers are the leading cause of death in animals and humans. The exact cause of cancer is not known, but links between certain activities such as smoking or exposure to carcinogens and the incidence of certain types of cancers and tumors has been shown by a number of researchers.

Many types of chemotherapeutic agents have been shown to be effective against cancers and tumor cells, but not all types of cancers and tumors respond to these agents. Unfortunately many of these agents also destroy normal cells. The exact mechanism for the action of these chemotherapeutic agents are not always known.

Despite advances in the field of cancer treatment the leading therapies to date are surgery, radiation and chemotherapy. Chemotherapeutic approaches are said to fight cancers that are metastasized or ones that are particularly aggressive. Such cytocidal or cytostatic agents work best on cancers with large growth factors, i.e., ones whose cells are rapidly dividing. To date, hormones, in particular estrogen, progesterone and testosterone, and some antibiotics produced by a variety of microbes, alkylating agents, and anti-metabolites form the bulk of therapies available to oncologists. Ideally cytotoxic agents that have specificity for cancer and tumor cells while not affecting normal cells would be extremely desirable. Unfortunately, none have been found and instead agents which target especially rapidly dividing cells (both tumor and normal) have been used.

Clearly, the development of materials that would target tumor cells due to some unique specificity for them would be a breakthrough. Alternatively, materials that were cytotoxic to tumor cells while exerting mild effects on normal cells would be desirable. It is believed that the phosphonoglycine derivatives in combination with chemotherapeutic agents can suppress and reduce the growth of cancer cells, including leukemia.

Therefore, it is an object of this invention to provide a pharmaceutical composition that is effective in both suppressing and inhibiting the growth of tumors and cancers in mammals.

It has been found that the N-phosphonoglycines are especially effective in suppressing the growth of the cancer, tumor, virus, or bacteria. The use of these N-phosphonoglycines in combination with other chemotherapeutic agents which are effective in destroying the tumor is a novel method of treatment.

More specifically, it is an object of this invention to provide an anti-cancer composition comprising a pharmaceutical carrier and an N-phosphonoglycine derivative and a chemotherapeutic agent as defined herein along with a method of treating such cancers.

These phosphonoglycines compositions along with potentiators are also effective against viruses. The phosphonoglycine compositions can be used to treat viral infections. Therefore, it is a further object of this invention to provide a method of treating viral infections such as herpes simplex, HIV, influenza and rhinoviruses.

These and other objects will become evident from the following detailed description of this inventions.

SUMMARY OF THE INVENTION

A pharmaceutical composition for treatment of mammals, and in particular, warm blooded animals and humans, comprising a pharmaceutical carrier and an effective amount of a chemotherapeutic agent and an anti-cancer compound selected from the group consisting of N-phosphonoglycine derivatives of the formula:

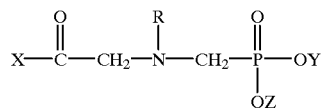

wherein

X is selected from the group consisting of hydroxy, alkoxy or chloroxy up to 12 carbon atoms; lower alkenoxy, cyclohexyloxy, morpholino, pyrrolidinyl, piperidino and NHR';

Y and Z each independently selected from hydrogen and lower alkyl; and

R is selected from the group consisting of hydrogen, formyl, acetyl, benzoyl, nitrobenzoyl and chlorinated benzoyl; and R' is selected from the group consisting of hydrogen, lower alkyl and lower alkenyl, cyclohexyl, phenalkyl of up to 8 carbon atoms, phenyl, chlorinated phenyl and anisyl; and certain salts of these compounds, which salts are selected from the group consisting of the Group I and II metals having an atomic number of up to 30, hydrochloride, acetate, solicylate, pyridine, ammonium, lower aliphatic hydrocarbon amine, lower alkanol amine and aniline.

These compositions can be used to inhibit the growth of cancers and other tumors in humans or animals by administration of an effective amount of the N-phosphonogylcine derivatives either orally, rectally, topically or parenterally, intravenously, or by direct injection near or into the tumor. Potentiators may be included in the compositions.

DETAILED DESCRIPTION OF THE INVENTION

A. Definitions:

As used herein, the term "comprising" means various components can be conjointly employed in the pharmaceutical composition of this invention. Accordingly, the terms "consisting essentially of" and "consisting of" are embodied in the term comprising.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. The specific "safe and effective amount" will, obviously, vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, a "pharmaceutical addition salts" includes a pharmaceutically acceptable salt of the anti-cancer compound with an organic or inorganic acid and the amine salts of the acid.

As used herein, a "pharmaceutical carrier" is a pharmaceutically acceptable solvent, suspending agent, liposome or vehicle for delivering the anti-cancer agent to the animal or human. The carrier may be liquid or solid and is selected with the planned manner of administration in mind.

As used herein, "cancer" refers to all types of cancers or neoplasm or tumors found in mammals, including leukemia.

As used herein, the "anti-cancer compounds" are the N-phosphonoglycines, and their salts. The exact N-phosphonoglycines are described in detail below. The preferred material is the products sold under the name glyphosate® or Roundup® by Monsanto. It is N-(phosphonomethyl) glycine.

As used herein, "viruses" includes viruses which cause diseases in warm blooded animals including HIV, influenza, rhinoviruses, herpes and the like.

As used herein "chemotherapeutic agents" includes DNA-interactive Agents, Antimetabolites, Tubulin-Interactive Agents, Hormonal agents and others, such as Asparaginase or hydroxyurea.

As used herein "potentiators" are materials such as triprolidine and its cis-isomer or procodazole which are used in combination with the chemotherapeutic agents and the phosphonoglycines.

B. The Anti-Cancer Compounds

The anti-cancer compounds are N-phosphonoglycine derivatives which are known for their herbicidal activities. They are systemic herbicides used to prevent and eradicate certain plants or weeds. Systemic herbicides are differentiated from other herbicides by their ability to move through the plant. It is not a requirement of this invention that the anti-cancer compounds have this ability.

The compounds have the following structure

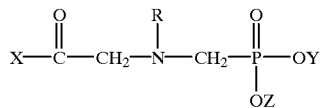

wherein
X is selected from the group consisting of hydroxy, thioyl, alkoxy or chloroxy up to 12 carbon atoms; lower alkenoxy, cyclohexyloxy, morpholino, pyrrolidinyl, piperidino and NHR';
Y and Z each independently selected from hydrogen and lower alkyl; and
R is selected from the group consisting of hydrogen, formyl, acetyl, benzoyl, nitrobenzoyl and chlorinated benzoyl; and
R' is selected from the group consisting of hydrogen, lower alkyl and lower alkenyl, cyclohexyl, phenalkyl of up to 8 carbon atoms, phenyl, chlorinated phenyl and anisyl; and certain salts of these compounds, which salts are selected from the group consisting of the Group I and II metals having an atomic number of up to 30, hydrochloride, pyridine, ammonium, lower aliphatic hydrocarbon amine, lower alkanol amine and aniline.

The most preferred compounds are those with the following structure:

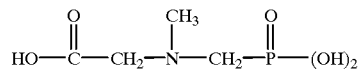

The lower alkylamine salts, in particular the isopropyl amine salts, are preferred.

These compounds are prepared according to the method described in U.S. Pat. No. 3,794,758 issued to Franz, Dec. 10, 1974.

C. Chemotherapeutic Agents

The chemotherapeutic agents are generally grouped as DNA-interactive Agents, Antimetabolites, Tubulin-Interactive Agents, Hormonal agents and others such as Asparaginase or hydroxyurea. Each of the groups of chemotherapeutic agents can be further divided by type of activity or compound. The chemotherapeutic agents used in combination with the phosphonoglycines of this invention include members of all of these groups. For a detailed discussion of the chemotherapeutic agents and their method of administration, see Dorr, et al, *Cancer Chemotherapy Handbook,* 2d edition, pages 15–34, Appleton & Lange (Connecticut, 1994) herein incorporated by reference.

DNA-Interactive Agents include the alkylating agents, e.g. Cisplatin, Cyclophosphamide, Altretamine; the DNA strand-breakage agents, such as Bleomycin; the intercalating topoisomerase II inhibitors, e.g., Dactinomycin and Doxorubicin); the nonintercalating topoisomerase II inhibitors such as, Etoposide and Teniposide; and the DNA minor groove binder Plicamycin.

The alkylating agents form covalent chemical adducts with cellular DNA, RNA, and protein molecules and with smaller amino acids, glutathione and similar chemicals. Generally, these alkylating agents react with a nucleophilic atom in a cellular constituent, such as an amino, carboxyl, phosphate, sulfhydryl group in nucleic acids, proteins, amino acids, or glutathione. The mechanism and the role of these alkylating agents in cancer therapy is not well understood. Typical alkylating agents include:

Nitrogen mustards, such as Chlorambucil, Cyclophosphamide, Isofamide, Mechlorethamine, Melphalan, Uracil mustard;

Aziridine such as Thiotepa methanesulphonate esters such as Busulfan;

nitroso ureas, such as Carmustine, Lomustine, Streptozocin;

platinum complexes, such as Cisplatin, Carboplatin;

bioreductive alkylator, such as Mitomycin, and Procarbazine, Dacarbazine and Altretamine;

DNA strand breaking agents include Bleomycin;

DNA topoisomerase II inhibitors include the following:
Intercalators, such as Amsacrine, Dactinomycin, Daunorubicin, Doxorubicin, Idarubicin, and Mitoxantrone;
nonintercalators, such as Etoposide and Teniposide.

The DNA minor groove binder is Plicamycin.

The antimetabolites interfere with the production of nucleic acids by one or the other of two major mechanisms. Some of the drugs inhibit production of the deoxyribonucleoside triphosphates that are the immediate precursors for DNA synthesis, thus inhibiting DNA replication. Some of the compounds are sufficiently like purines or pyrimidines to be able to substitute for them in the anabolic nucleotide pathways. These analogs can then be substituted into the DNA and RNA instead of their normal counterparts. The antimetabolites useful herein include:

folate antagonists such as Methotrexate and trimetrexate pyrimidine antagonists, such as Fluorouracil, Fluorodeoxyuridine, CB3717, Azacitidine, Cytarabine, and Floxuridine purine antagonists include Mercaptopurine, 6-Thioguanine, Fludarabine, Pentostatin;

sugar modified analogs include Cyctrabine, Fludarabine;

ribonucleotide reductase inhibitors include hydroxyurea.

Tubulin Interactive agents act by binding to specific sites on tubulin, a protein that polymerizes to form cellular microtubules. Microtubules are critical cell structure units. When the interactive agents bind on the protein, the cell can not form microtubules Tubulin Interactive agents include Vincristine and Vinblastine, both alkaloids and Paclitaxel.

Hormonal agents are also useful in the treatment of cancers and tumors. They are used in hormonally susceptible tumors and are usually derived from natural sources. These include:

estrogens, conjugated estrogens and Ethinyl Estradiol and Diethylstilbesterol, Chlortrianisen and Idenestrol;

progestins such as Hydroxyprogesterone caproate, Medroxyprogesterone, and Megestrol;

androgens such as testosterone, testosterone propionate; fluoxymesterone, methyltestosterone;

Adrenal corticosteroids are derived from natural adrenal cortisol or hydrocortisone. They are used because of their anti inflammatory benefits as well as the ability of some to inhibit mitotic divisions and to halt DNA synthesis. These compounds include, Prednisone, Dexamethasone, Methylprednisolone, and Prednisolone.

Leutinizing hormone releasing hormone agents or gonadotropin-releasing hormone antagonists are used primarily the treatment of prostate cancer. These include leuprolide acetate and goserelin acetate. They prevent the biosynthesis of steroids in the testes.

Antihomional antigens include:

antiestrogenic agents such as Tamosifen, antiandrogen agents such as Flutamide; and antiadrenal agents such as Mitotane and Aminoglutethimide.

Hydroxyurea appears to act primarily through inhibition of the enzyme ribonucleotide reductase.

Asparagenase is an enzyme which converts asparagine to nonfunctional aspartic acid and thus blocks protein synthesis in the tumor.

D. Potentiators

The "potentiators" can be any material which improves or increase the efficacy of the pharmaceutical composition or which act on the immune system. One such potentiator is triprolidine and its cis-isomer which are used in combination with the chemotherapeutic agents and the N-phosphonoglycine derivative. Triprolidine is described in U.S. Pat. No. 5,114,951 (1992).

Another potentiator is procodazole, 1H-Benzimidazole-2-propanoic acid; [β-(2-benzimidazole]propionic acid; 2-(2-carboxyethyl)benzimidazole; propazol]. Procodazole is a non-specific active immunoprotective agent against viral and bacterial infections and can be used with the compositions claimed herein. It is effective with the N-phosphonoglycines alone in treating cancers, tumors, leukemia and viral infections or when combined with N-phosphonoglycine derivatives and chemotherapeutic agents.

Propionic acid and its salts and esters can also be used in combination with the pharmaceutical compositions claimed herein.

Antioxidant vitamins such as vitamins A, C and E and beta-carotene can be added to these compositions.

E. Dosage

Any suitable dosage may be given in the method of the invention. The type of compound and the carrier and the amount will vary widely depending on the species of the warm blooded animal or human, body weight, and tumor being treated. For the chemotherapeutic agents a lower dosage of from 0.5 mg/kg body weight to about 400 mg/kg body weight is acceptable. Generally a dosage of between about 2 milligrams (mg) per kilogram (kg) of body weight and about 400 mg per kg of body weight is suitable. However, high dosages may be used, up to 1000 mg/kg. Preferably from 15 mg to about 150 mg/kg of body weight is used. Generally, the dosage in man is lower than for small warm blooded mammals such as mice. A dosage unit may comprise a single compound or mixtures thereof with other compounds or other cancer inhibiting compounds. The exact range and ratio of the chemotherapeutic agent to the N-phosphonoglycine will depend on the type of chemotherapeutic agent and the cancer being treated. The dosage unit can also comprise diluents, extenders, carriers and the like. The unit may be in solid or gel form such as pills, tablets, capsules and the like or in liquid form suitable for oral, rectal, topical or parenteral administration or intravenous administration or injection into or around the tumor site.

F. Dosage Delivery Forms

The anti-cancer compounds and chemotherapeutic agent and optionally the potentiator, are typically mixed with a pharmaceutically acceptable carrier. This carrier can be a solid or liquid or liposome and the type is generally chosen based on the type of administration being used. The active agent can be coadministered in the form of a tablet or capsule, as an agglomerated powder or in a liquid form. Examples of solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of liquid dosage forms include solutions or suspensions in water, pharmaceutically acceptable fats and oils, alcohols or other organic solvents, including esters, emulsions, syrups, elixirs, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners and melting agents. Oral dosage forms would contain flavorants and coloring agents. Parenteral and intravenous forms would also include minerals and other materials to make them compatible with the type of injection or delivery system chosen.

Specific examples of pharmaceutical acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described in the following references: 7 *Modern Pharmaceutics,* Chapters 9 and 10 (Banker & Rhodes, Editors, 1979); Lieberman et al., *Pharmaceutical Dosage Forms: Tablets* (1981); and Ansel, *Introduction to Pharmaceutical Dosage Forms* 2nd Edition (1976).

G. Method of Treatment

The method of treatment can be any suitable method which is effective in the treatment of the particular virus, cancer or tumor type that is being treated. Treatment may be oral, rectal, topical, parenteral, intravenous or injection into or around the tumor site and the like. The method of applying an effective amount also varies depending on the tumor being treated. It is believed that parenteral treatment by intravenous, subcutaneous, or intramuscular application, formulated with an appropriate carrier, additional cancer inhibiting compound or compounds or diluent to facilitate application will be the preferred method of administering the compounds to warm blooded animals.

It is believed that many herbicides alone or in combination with other herbicides and/or fungicides will show this beneficial anti-tumor effect. Preferred fungicides include the benzimidazole fungicides such as carbendazim, thiabendazole, benomyl. Other agents which can be used include griseofulvin, fluconazole and propiconazole.

The N-phosphonoglycine derivatives are also effective against viruses including rhinovirus, HIV, herpes, and influenza. The combination of the N-phosphonoglycines with potentiators are especially effective against viruses. The dosage form and method of treatment is the same as for tumors or cancer.

H. Anti-Viral Evaluation with Herpes Simplex

Female CD (mice Charles River Breeding Laboratories, Portage, Mich.) 5 to 7 weeks old of age at the time of receipt are used. Mice are approximately 6 to 9 weeks old and weigh approximately 20 to 28 grams at the time test initiation. All mice used in the study do not vary in age by more than 10 days. The mice are housed 6 per cage with bedding. The mice are fed rodent diet 5002 (PMI, St. Louis Mo.) ad libitum. Fresh water is supplied to the mice ad libitum.

Herpes Simplex Virus, type 2, strain MS, is used to challenge the mice. The virus is stored and thawed and administered to the mice. The organism is stored at approximately −70° C. Prior to infectious challenge a vial of frozen stock is thawed and diluted to the appropriate concentration in buffered saline solution. The mice are anesthetized with Halothane and the virus challenge dose is administered intra-nasally in volume of 50 microliters.

Glyphosate, N-(phosphonomethyl)glycine isopropyl amine salt, is administered at a concentration 150 mg/kg of body weight. Acyclovir is also administered to a set of mice at 75 mg/kg body weight. On days 1 through 14, 10 mice per group receive the composition by oral lavage. Saline control animals (10) receive a comparable volume of saline as compared to the test article-dosed mice. Test composition dosing is accomplished at approximately 24 hour intervals. On day 0 approximately 4 hours after the second dosing of test articles or saline, all mice are challenged intra-nasally with an infective dose of virus calculated to produce approximately 90% lethality. Animals are observed daily for 21 days after infectious challenge for mortality or moribundity. Test animals are observed twice after dosing on day 1, three times on day 0 and twice daily thereafter.

The mice begin treated with Glyphosate and acylcovir both had a 60% survival rate. The untreated control group had a 20% survival rate.

What is claimed is:

1. A pharmaceutical composition for treating cancers or tumors or viral infections comprising a pharmaceutically acceptable carrier and a safe and effective amount of a chemotherapeutic agent and a safe and effective amount of an N-phosphonoglycine derivative of the formula:

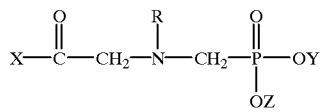

wherein
X is selected from the group consisting of hydroxyl, alkoxy or chloroxyl up to 12 carbon atoms, lower alkenoxy, cyclohexyloxy, morpholino, pyrrolidinyl, piperidino and NHR';
Y and Z each independently selected from hydrogen and lower alkyl; and R is selected from the group consisting of hydrogen, formyl, acetyl, benzoyl, nitrobenzoyl and chlorinated benzoyl; and
R' is selected from the group consisting of hydrogen, lower alkyl and lower alkenyl, cyclohexyl, phenalkyl of up to 8 carbon atoms, phenyl, chlorinated phenyl and anisyl; and certain salts of these compounds, which salts are selected from the group consisting of the Group I and II metals having an atomic number of up to 30, hydrochloride, acetate, salicylate, pyridine, ammonium, lower aliphatic hydrocarbon amine, lower alkanol amine and aniline.

2. A pharmaceutical composition according to claim 1 comprising a pharmaceutically acceptable carrier and a safe and effective amount of a N-(phosphonomethyl) glycine or an isopropyl amine salt thereof.

3. A pharmaceutical composition according to claim 1 wherein said salts are selected from the group consisting of hydrochloride, acetate, salicylate, lower alkyl amine and mixtures thereof.

4. A pharmaceutical composition according to claim 1 wherein said chemotherapeutic agent is selected from the group consisting of Asparaginase, hydroxyurea, Cisplatin, Cyclophosphamide, Altretamine, Bleomycin, Dactinomycin, Doxorubicin, Etoposide, Teniposide, and Plicamycin.

5. A pharmaceutical composition according to claim 4 wherein said chemotherapeutic agent is selected from the group consisting of Methotrexate, Fluorouracil, Fluorodeoxyuridine, CB3717, Azacitidine, Cytarabine, Floxuridine, Mercaptopurine, 6-Thioguanine, Fludarabine, Pentostatin, Cyctrabine, and Fludarabine.

6. A pharmaceutical composition according to claim 4 which further comprises a potentiator.

7. A method of treating cancer in warm blooded mammals comprising administering a safe and effective amount of a pharmaceutical composition comprising a chemotherapeutic agent and an N-phosphonoglycine derivative of the formula:

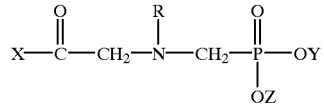

wherein
X is selected from the group consisting of hydroxyl, alkoxy or chloroxy up to 12 carbon atoms, lower alkenoxy, cyclohexyloxy, morpholino, pyrrolidinyl, piperidino and NHR';
Y and Z each independently selected from hydrogen and lower alkyl; and
R is selected from the group consisting of hydrogen, formyl, acetyl, benzoyl, nitrobenzoyl and chlorinated benzoyl; and
R' is selected from the group consisting of hydrogen, lower alkyl and lower alkenyl, cyclohexyl, phenalkyl of up to 8 carbon atoms, phenyl, chlorinated phenyl and anisyl; and certain salts of these compounds, which salts are selected from the group consisting of the Group I and II metals having an atomic number of up to 30, hydrochloride, salicylate, acetate, pyridine, ammonium, lower aliphatic hydrocarbon amine, lower alkanol, amine and aniline.

8. A method of treating cancer in warm blooded mammals according to claim 7 comprising administering a safe and effective amount of a N-(phosphonomethyl) glycine.

9. A method according to claim 8 wherein from about 2 mg/kg body weight to about 400 mg/kg of said N-(phosphonomethyl) glycine is administered.

10. A method according to claim 7 wherein said chemotherapeutic agent is selected from the group consisting of DNA-interactive Agents, Antimetabolites, Tubulin-Interactive Agents, Hormonal agents, Asparaginase and hydroxyurea.

11. A method according to claim 10 wherein said chemotherapeutic agent is selected from the group consisting of Asparaginase, hydroxyurea, Cisplatin, Cyclophosphamide, Altretamine, Bleomycin, Dactinomycin, Doxorubicin, Etoposide, Teniposide, and Plicamycin.

12. A method according to claim 11 wherein said chemotherapeutic agent is selected from the group consisting of Methotrexate, Fluorouracil, Fluorodeoxyuridine, CB3717, Azacitidine, Cytarabine, Floxuridine, Mercaptopurine, 6-Thioguanine, Fludarabine, Pentostatin, Cyctrabine, and Fludarabine.

13. A method according to claim 12 wherein said N-phosphonoglycine is a N-(phosphonomethyl) glycine isopropyl amine salt.

14. A unit dosage composition for treating tumors or viral infections comprising a safe and effective amount of a chemotherapeutic agent, an N-phosphonoglycine derivative of the formula:

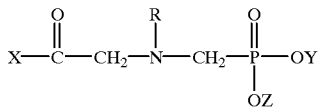

wherein

X is selected from the group consisting of hydroxyl, alkoxy or chloroxyl up to 12 carbon atoms, lower alkenoxy, cyclohexyloxy, morpholino, pyrrolidinyl, piperidino and NHR';

Y and Z each independently selected from hydrogen and lower alkyl; and

R is selected from the group consisting of hydrogen, formyl, acetyl, benzoyl, nitrobenzoyl and chlorinated benzoyl, and R' is selected from the group consisting of hydrogen, lower alkyl and lower alkenyl, cyclohexyl, phenalkyl of up to 8 carbon atoms, phenyl, chlorinated phenyl and anisyl; and certain salts of these compounds, which salts are selected from the group consisting of the Group I and II metals having an atomic number of up to 30, hydrochloride, pyridine, ammonium, lower aliphatic hydrocarbon amine, lower alkanol amine and aniline, and a pharmaceutically acceptable carrier.

15. A unit dosage composition according to claim 14 wherein said N-phosphonoglycine is N-(phosphonomethyl) glycine or a lower alkyl amine salt thereof.

16. A unit dosage composition according to claim 14 wherein said salts are selected from the group consisting of hydrochlorides, acetates, salicylates, and mixtures thereof.

17. A safe and effective treatment for viral infections comprising administering a safe and effective amount of a pharmaceutical composition comprising an N-phosphonoglycine derivative of the formula:

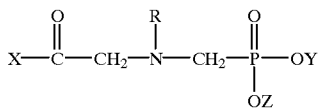

wherein

X is selected from the group consisting of hydroxyl, alkoxy or chloroxy up to 12 carbon atoms, lower alkenoxy, cyclohexyloxy, morpholino, pyrrolidinyl, piperidino and NHR';

Y and Z each independently selected from hydrogen and lower alkyl; and

R is selected from the group consisting of hydrogen, formyl, acetyl, benzoyl, nitrobenzoyl and chlorinated benzoyl; and R' is selected from the group consisting of hydrogen, lower alkyl and lower alkenyl, cyclohexyl, phenalkyl of up to 8 carbon atoms, phenyl, chlorinated phenyl and anisyl; and a safe and effective amount of a potentiator.

18. A treatment according to claim 17 wherein said N-phosphonoglycine is administered orally or enterically or intravenously.

19. A treatment according to claim 17 wherein said N-phosphonoglycine is administered in a solid form.

20. A treatment according to claim 19 wherein said solid form includes a carrier selected from the group consisting of lactose, sucrose, gelatin and agar.

21. A treatment according to claim 20 wherein from about 15 mg/kg to about 150 mg/kg of said N-phosphonoglycine is administered.

22. A treatment according to claim 17 wherein said potentiator is procodazole.

23. A unit dosage composition for inhibiting the growth of tumors comprising a safe and effective amount of a systemic herbicide, a fungicide and a chemotherapeutic agent.

24. A unit dosage composition according to claim 23 which additionally comprises a potentiator.

25. A safe and effective treatment for herpes viral infections comprising administering a safe and effective amount of a pharmaceutical composition comprising an N-phosphonoglycine derivative of the formula:

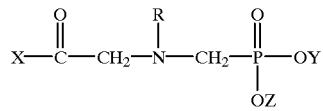

wherein

X is selected from the group consisting of hydroxyl, alkoxy or chloroxy up to 12 carbon atoms, lower alkenoxy, cyclohexyloxy, morpholino, pyrrolidinyl, piperidino and NHR';

Y and Z each independently selected from hydrogen and lower alkyl; and

R is selected from the group consisting of hydrogen, formyl, acetyl, benzoyl, nitrobenzoyl and chlorinated benzoyl; and R' is selected from the group consisting of hydrogen, lower alkyl and lower alkenyl, cyclohexyl, phenalkyl of up to 8 carbon atoms, phenyl, chlorinated phenyl and anisyl.

26. A treatment according to claim 25 wherein said N-phosphonoglycine is N-(phosphonomethyl)glycine or a lower alkyl amine salt thereof.

* * * * *

UNITED STATES PATENT AND TRADEMARK OFFICE
CERTIFICATE OF CORRECTION

PATENT NO. : 6,090,796
DATED : July 18, 2000
INVENTOR(S) : James Berger Camden

It is certified that error appears in the above-identified patent and that said Letters Patent is hereby corrected as shown below:

Claim 1,
Column 7, line 63, and in claim 14, column 9, line 32, delete "chloroxyl" and insert in lieu thereof -- chloroalkoxy --.
Column 7, line 66, claim 7, column 8, line 48, claim 14, column 9, line 35, claim 17, column 10, line 5, and in claim 25, column 10, line 51, immediately after 'Z', insert -- are --.

Claim 5,
Column 8, line 30, and in claim 12, column 9, lines 14-15, delete "Cyctrabine, and Fludarabine".
Column 8, line 29, and in claim 12, column 9, line 14, immediately after 'Fludarabine,' insert -- and --.

Claim 7,
Column 8, line 45, claim 17, column 10, line 2, and claim 25, column 10, line 48, delete "chloroxyl" and insert in lieu thereof -- chloroalkoxy --.
Column 8, line 61, delete the comma "," after 'alkanol'.

Signed and Sealed this

Twenty-seventh Day of November, 2001

Attest:

NICHOLAS P. GODICI
*Attesting Officer*     *Acting Director of the United States Patent and Trademark Office*